United States Patent [19]

Richter

[11] 4,230,104
[45] Oct. 28, 1980

[54] SPLINTS FOR TREATING JAW FRACTURES

[76] Inventor: Alice E. Richter, 260 N. Cache St., Jackson, Wyo. 83001

[21] Appl. No.: 871,642

[22] Filed: Jan. 23, 1978

[51] Int. Cl.$^2$ .............................................. A61F 5/04
[52] U.S. Cl. .................................. 128/89 A; 433/19
[58] Field of Search ...................... 32/14 A; 128/89 A

[56] References Cited

U.S. PATENT DOCUMENTS

| | | | |
|---|---|---|---|
| 1,638,006 | 8/1927 | Aderer | 32/14 A |
| 2,502,902 | 4/1950 | Tofflemire | 32/14 A |
| 3,474,779 | 10/1969 | Wall, Jr. | 32/14 A |
| 3,618,214 | 11/1971 | Armstrong | 32/14 A |

FOREIGN PATENT DOCUMENTS 285160  1/1971  U.S.S.R. ................................. 128/89 A

*Primary Examiner*—Louis G. Mancene
*Assistant Examiner*—John J. Wilson
*Attorney, Agent, or Firm*—James J. Conlon

[57] ABSTRACT

An orthodontic appliance comprising a bar that provides a splint for setting broken jaws or other facial bones. Upper and lower bars are attached to the patient's teeth with ligature wires and interconnected with the elastic bands to allow the jaw to set properly. The elastic bands are mounted within a prong that provides a base surface to receive the elastic band and has a movable tab member to thereby provide an enclosed opening to receive and hold each band. After the bands are positioned the associated movable tab is bent over the elastic band to hold it in place and provide a rounded contour that matches the tissue of the gum. The prongs can be easily bent for attachment of ligature wires from any direction to support other facial bones which are to set.

2 Claims, 5 Drawing Figures

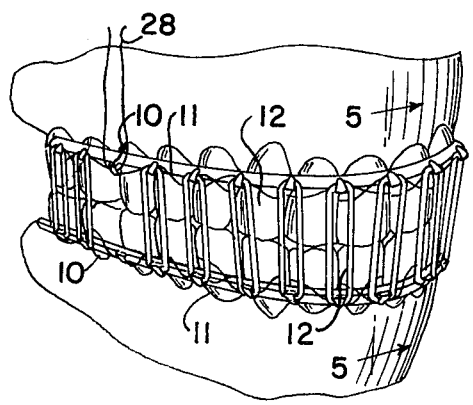
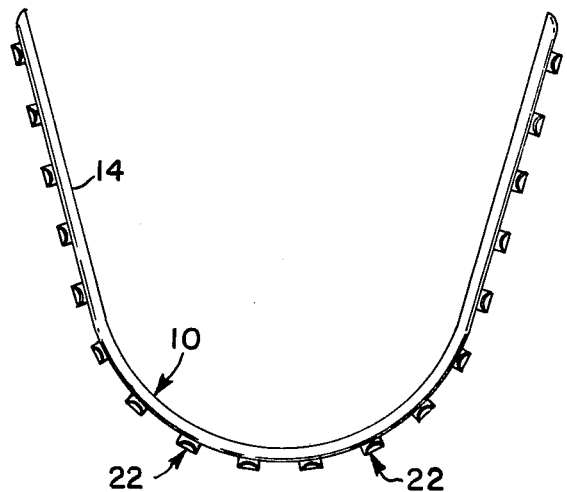
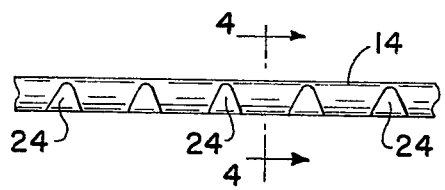
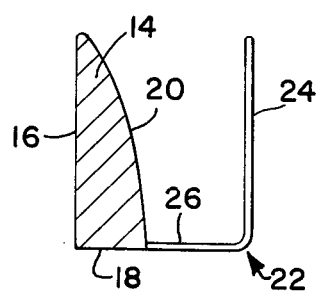
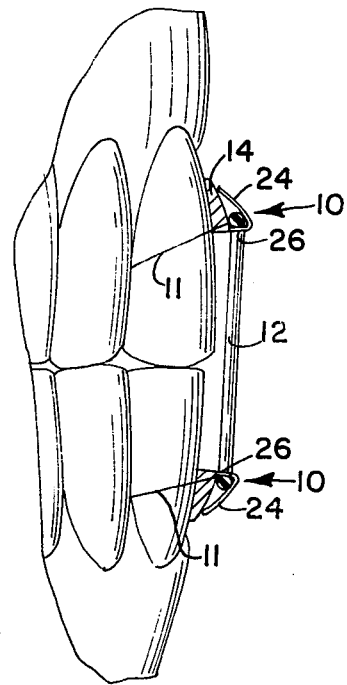

4,230,104

SPLINTS FOR TREATING JAW FRACTURES

BACKGROUND OF THE INVENTION (1) Field of the Invention

This invention pertains to an orthodontic or dental device sometimes called a fracture splint that may be attached to a person's upper and lower teeth and interconnected in order to provide for setting and proper healing of fractures of the mandible and/or maxilla, otherwise known as a broken jaw.

(2) Description of the Prior Art

The prior art discloses several splints for treating fractures of the jaw. The fractured splint is closed in the Adderer, U.S. Pat. No. 1,638,006 (1927), showing a typical splint which is widely used by orthodontists. The Adderer device discloses a number of upwardly disposed loops 15 that are used as attachment points for elastic bands. Loops 15 are attached outwardly of the associated band 11 and extend vertically when positioned in a person's mouth. This arrangement is effective yet can be uncomfortable because the loops 15 do not conform to the natural contours of teeth or gums and can create a feeling of having a foreign member in one's mouth. Further, these loops present a danger of irritating open lacerations which often accompany facial injuries. The loops also present a number of crevices that can harbour food particles which can create bacteria and necessitate unusual number of cleansing operations during the day in order that infections or offensive tastes do not develop. Further, loops 15 of Adderer are extremely rigid and cannot be bent easily backward to hold the elastic band in place which may be required when used on children or others who are inclined to remove the bands.

Other limitations are encountered with prior art devices when it becomes necessary to utilize wiring between facial bones and one of the fracture splints. For example, when horizontal fractures occur it oftentimes becomes necessary to wire facial bones to the teeth attached fracture splints. Because common splints attached to upper teeth have loops extending vertically upward, it is difficult to loop wires around the lugs and sometimes makes it necessary to remove the splint, and re-attach it with the lugs extending downwardly because the lugs cannot be bent in a different direction. The splint disclosed herein provides lugs which may be utilized in a multitude of applications and solves the problems associated with prior devices.

SUMMARY OF THE INVENTION

This invention pertains to an orthodontic device and in particular to a so-called splint that is used in setting broken jaws or broken facial bones.

In use, splints are attached to the upper and lower teeth of the person having a broken jaw to set. Each splint is wired by ligature wires to a person's teeth and, subsequently, interconnected by short elastic bands which extend over prongs and thus draw the upper and lower teeth together to allow the broken jaw to set in a natural position. After the elastic bands are positioned over the associated prongs, tabs are bend backwards to provide a smooth contoured member that not only holds the elastic bands in place but also provides a smooth contour tab that matches the contours of the teeth and surrounding gums to prevent irritation of adjacent tissue.

In the event facial bones are broken in such a manner that it is necessary to wire the bones to a teeth attached splint, it is not necessary to remove the splint and turn it upside down in order to orient prongs in such a direction to receive the home setting wires. With use of the splint disclosed herein, the prongs may be bent in a direction to provide for attachment of wires as needed.

It is thus an object to disclose an improved orthodontic appliance or fracture splint that is easy to attach to a person suffering from a broken jaw or broken facial bones and which can be interconnected to an associated splint with an elastic band so that they are firmly held in place when movable tabs are positioned over the elastic bands.

It is another object to disclose an improved splint having an arch bar that may be fitted about a person's teeth and provide a number of outwardly extended tabs. The bar can be adjusted to provide a contour that is unobtrusive and conforms with the adjacent gums and teeth of the patient.

It is yet another object to disclose an improved fracture splint having prongs which may be bent as required for attachment of wires used to set broken facial bones.

These and other objects of the invention will become apparent to those having ordinary skill in the art with reference to the following drawings, description and claims.

BRIEF DESCRIPTION OF THE DRAWINGS

FIG. 1 is a pictorial illustration of a fracture splint in position in a person's mouth and attached to the person's teeth;

FIG. 2 is a top plan view of the splint disclosed herein;

FIG. 3 is a front elevational view of the arched bar shown in FIG. 2;

FIG. 4 is a sectional view taken generally along line 4—4 of FIG. 3; and,

FIG. 5 is a sectional view taken generally along line 5—5 of FIG. 1.

DETAILED DESCRIPTION OF THE DRAWINGS

In setting broken jaws or other broken facial bones, the bones are manually manipulated back into a correct position for setting. However, because of comfort problems a cast cannot be placed upon the head and face area for holding bones in place for setting and because a jaw cannot accurately be set by use of a cast alone, it becomes necessary to wire an injured person's teeth together to allow the jaw or other broken facial bone to set in a natural manner. After the teeth are locked together, the jaw bones and facial bones assume their natural position and setting of the bones can and should occur. The device described herein is attached to teeth in a highly efficient and safe manner and has prongs that can be easily bent to accommodate interconnection with another splint or connection with wires used to hold broken facial bones in place.

Referring now to the drawings and in particular to FIG. 1, we are shown a pair of splints 10 adapted and attached to the upper and lower teeth by ligatures or wires 11. In such a position, the splints 10 are firmly held to the wearer's teeth because the wires 11 are woven around and about the wearer's teeth and over an adjacent area of the splint 10. Elastic bands 12 are interconnected to each splint to firmly urge the teeth together in position to provide for a natural setting of a broken jaw.

Each splint 10, as shown in FIGS. 3–5, comprises a so-called arch bar 14 which is made for a malleable dental metal or other suitable material that is easily curved to conform with the contour of the wearer's teeth. Bars 14 are in the order of 145 mm in length. As shown in FIG. 4, the bars 14 have a flat back section 16 which is adjacent to the wearer's teeth and is in the order of 3 mm in height. Extending from the upstanding back 16 is a short bottom 18 approximately 1 mm. A curved front 20 interconnects the extreme portion of the back 16 and the bottom 18.

Prong 22 extends from the lower portion of bar 14 and generally in a plane with the bottom 18. Prong 22 has a movable tab 24 and a base section 26 having a length of about 1.5 mm. Prong 22 is in the order of 3 mm in length.

The tab 24 of prong 22 has a triangular shape as viewed in FIG. 3 which allows elastic bands 12 and ligature wires 11 to be easily attached. Similarly, when bent downwardly, the triangular shape makes attachment of suspensary wires 28 easier to accomplish.

Splint 10 may be formed from a single bar to which a number of prongs 22 are attached as by soldering, or may be formed as a single unit having prongs 22 formed integrally therewith.

As shown in FIG. 5, after the splints are wired to the wearer's teeth, elastic bands 12 are located over tabs 24 in such a fashion as to be seated on their associated base 26. Once in this position, the tabs 24 may be turned or bent towards the wearer's teeth in contact with curved front 20 to prevent the elastic bands from being removed. Tabs 24 may be bent back to provide a small opening between tabs 24 and the curved front 20 in such a manner as to provide a smooth contour yet allow the elastic bands 12 to be easily removed. It is contemplated that all the tabs 24 are bent backwards to some degree, in order to provide a smooth contoured member within the wearer's mouth that does not cause irritation to adjacent tissue.

As shown in FIG. 1, prongs 22 may be bent away from the curved front 24 in such a manner to allow for attachment of so-called suspensary wires 28 to hold upper facial bones in position for setting. Thus splint 10 provides prongs which may be disposed or bent in various directions and used in interconnecting splints 10 or used in attaching suspensary wires 28.

The foregoing description and drawings merely explain and illustrate the invention and the invention is not limited thereto, except insofar as the appended claims are so limited, as those who are skilled in the art and have the disclosure before them will be able to make modifications and variations therein without departing from the scope of the invention.

What is claimed is:

1. An oral surgery appliance for use in holding together human jaws to permit the jaws by wires and elastic bands to set properly, the improvements comprising:
    a malleable arch bar member;
    said arch bar member having metal means adapted to be shaped into a curved configuration about a person's teeth and conform to the contour thereof;
    said arch bar having flat back for positioning adjacent the wearer's teeth and also having an arcuate front extending downwardly from the top of the flat back;
    prong means;
    said prong having base means extending horizontally from said bar member;
    tab means including a first portion extending from said base member;
    said tab means including means movable by bending from a first position spaced from the arch bar member to a second position with a portion of said tab adjacent to the arch bar member yet shorter than the contiguous portion of the arch bar member to provide a smooth contour; and
    said means movable by bending comprising means adapted to extend away from said arch bar member and confine and hold said elastic bands.

2. The oral surgery appliance of claim 1, and:
    said tab means having a triangular shape comprising sides extending from said base to an apex.

* * * * *